US012653431B2

(12) United States Patent　　　　(10) Patent No.:　US 12,653,431 B2
Takeuchi et al.　　　　　　　　　　(45) Date of Patent:　　Jun. 16, 2026

(54) BLOOD COLLECTION INSTRUMENT AND BLOOD COLLECTION PLATE

(71) Applicants:SHIMADZU CORPORATION, Kyoto (JP); NIPRO CORPORATION, Osaka (JP); HUNDRED CO., LTD., Koriyama (JP)

(72) Inventors: Ippei Takeuchi, Kyoto (JP); Hiroyuki Nakagami, Osaka (JP); Tatsuya Kudo, Osaka (JP); Takashi Eshima, Osaka (JP); Naoyuki Kayamoto, Koriyama (JP); Makoto Murakami, Koriyama (JP)

(73) Assignees: SHIMADZU CORPORATION, Kyoto (JP); NIPRO CORPORATION, Osaka (JP); HUNDRED CO., LTD., Koriyama (JP)

( * ) Notice: Subject to any disclaimer, the term of this patent is extended or adjusted under 35 U.S.C. 154(b) by 546 days.

(21) Appl. No.: 18/024,382

(22) PCT Filed: Sep. 2, 2021

(86) PCT No.: PCT/JP2021/032296
§ 371 (c)(1),
(2) Date: Mar. 2, 2023

(87) PCT Pub. No.: WO2022/050350
PCT Pub. Date: Mar. 10, 2022

(65) Prior Publication Data
US 2024/0023852 A1　　Jan. 25, 2024

(30) Foreign Application Priority Data
Sep. 3, 2020　(JP) ................................. 2020-148117

(51) Int. Cl.
*A61B 5/15* 　　　　(2006.01)

(52) U.S. Cl.
CPC .... *A61B 5/150251* (2013.01); *A61B 5/15003* (2013.01); *A61B 5/150213* (2013.01);
(Continued)

(58) Field of Classification Search
CPC .......... A61B 5/150251; A61B 5/15003; A61B 5/150213; A61B 5/150389; A61B 5/15074
See application file for complete search history.

(56) References Cited

U.S. PATENT DOCUMENTS

2019/0011334 A1* 　1/2019　Takeuchi ......... A61B 5/150213

FOREIGN PATENT DOCUMENTS

| JP | 3226487 U | 7/2020 |
| WO | 2017/122314 A1 | 7/2017 |

(Continued)

OTHER PUBLICATIONS

Jul. 17, 2024 extended Search Report issued in European Patent Application No. 21864403.7.
(Continued)

*Primary Examiner* — Daniel L Cerioni
(74) *Attorney, Agent, or Firm* — Oliff PLC

(57) ABSTRACT

A blood collection instrument includes a blood holding member with a structure in which a plurality of plate-shaped members are overlapped with each other and a collected blood holding passage formed between overlapped surfaces of the plate-shaped members; a connection part provided at an inflow port of the collected blood holding passage in the blood holding member; and a puncture member with a puncturing hollow needle connected to the connection part. An inner hole of the hollow needle of the puncture member is allowed to communicate with the collected blood holding passage in the blood holding member.

4 Claims, 10 Drawing Sheets

(52) U.S. Cl.
    CPC .... *A61B 5/150389* (2013.01); *A61B 5/15074*
            (2013.01); *A61B 2560/0406* (2013.01)

(56)            References Cited

FOREIGN PATENT DOCUMENTS

| WO | 2017/122372 A1 | 7/2017 |
| WO | 2020/158929 A1 | 8/2020 |

OTHER PUBLICATIONS

Nov. 22, 2021 International Search Report issued in Patent Application No. PCT/JP2021/032296.

Mar. 7, 2023 International Preliminary Report on Patentability issued in International Application No. PCT/JP2021/032296.

Mar. 28, 2024 Offie Action issued in Japanese Patent Application No. 2020-148117.

May 29, 2025 Office Action issued in Chinese Patent Application No. 202180054100.0.

Dec. 31, 2025 Office Action issued in Chinese Patent Application No. 202180054100.0.

\* cited by examiner

BLOOD COLLECTION INSTRUMENT AND BLOOD COLLECTION PLATE

TECHNICAL FIELD

The present invention relates to a blood collection instrument and a blood collection plate that are used for collecting a predetermined amount of blood from a small animal or the like.

BACKGROUND ART

Conventionally, as a kind of blood collection instrument, a blood collection device is known as described in WO 2017/122372 (Patent Document 1). The blood collection device has a thin collected blood passage between the overlapped surfaces of a plurality of plate-shaped members and is configured to collect and hold a minute quantity of blood by using capillarity or the like. The blood collection device having the conventional structure described in Patent Document 1 collects blood by bringing the collection port of the tip of the collected blood passage into direct contact with a drop of blood (blood shaped like a ball by surface tension) obtained on a skin by pin needling on a skin of a small animal or the like and sucking the drop of blood by capillarity.

BACKGROUND ART DOCUMENT

Patent Document

Patent Document 1: WO 2017/122372 A1

SUMMARY OF THE INVENTION

Problem the Invention Attempts to Solve

However, the above-mentioned blood collection method cannot avoid a state like atmospheric oxidization of blood because blood is exposed to the outside before being collected. Thus, the blood collection method is not suitable for analysis affected by oxidation reaction and thus may limit the applications of analysis.

It is an object of the present invention to provide a new blood collection instrument that is improved to make it difficult to expose collected blood to the atmosphere.

It is also an object of the present invention to provide a new blood collection plate properly used for the blood collection instrument.

Means for Solving the Problem

Hereinafter, preferred embodiments for grasping the present invention will be described. However, each preferred embodiment described below is exemplary and can be appropriately combined with each other. Besides, a plurality of elements described in each preferred embodiment can be recognized and adopted as independently as possible, or can also be appropriately combined with any element described in other preferred embodiments. Hence, in the present invention, various other preferred embodiments can be realized without being limited to those described below.

A first preferred embodiment provides a blood collection instrument comprising: a blood holding member having a structure in which a plurality of plate-shaped members are overlapped with each other, the blood holding member including a collected blood holding passage formed between overlapped surfaces of the plurality of plate-shaped members; a connection part provided at an inflow port portion of the collected blood holding passage in the blood holding member; and a puncture member including a hollow needle for puncture, the puncture member being connected to the connection part, wherein an inner hole of the hollow needle of the puncture member is allowed to communicate with the collected blood holding passage of the blood holding member.

According to the blood collection instrument of the present preferred embodiment, the puncture member having the hollow needle is provided on the blood collection port (inflow port) side of the collected blood holding passage in the blood holding member, so that blood collected from the body of a small animal or the like with the hollow needle can be directly guided into the collected blood holding passage of the blood holding member. Thus, even if the blood holding member has the collected blood holding passage between the overlapped surfaces of the plurality of plate-shaped members, problems such as exposure of blood to the atmosphere during collection and oxidization associated with the exposure can be reduced or avoided.

A second preferred embodiment provides the blood collection instrument according to the first preferred embodiment, wherein the connection part projects outward, and a connection linking part on a hollow needle side that is connected to be fit externally onto the connection part has flexibility.

According to the blood collection instrument of the present preferred embodiment, for example, even if an external force is applied with a hand or the like to the plate-shaped blood holding member at the time of puncture on a small animal with the hollow needle, it is difficult for the external force to be transmitted to the puncture member because of the deformation of the connection linking part.

The connection linking part of the puncture member deforms according to the shape of the outer circumferential surface of the connection part, thereby easily linking the puncture member and the blood holding member. In addition, it is difficult for a gap to be formed between the connection linking part and the connection part, thereby reducing or preventing leakage of blood from a gap at a connected portion between the puncture member and the blood holding member when being affected by a blood pressure or the like.

A third preferred embodiment provides the blood collection instrument according to the first or second preferred embodiment, wherein at least one of an outer circumferential surface and an inner circumferential surface of the connection part is circular in cross section.

According to the blood collection instrument of the present preferred embodiment, at least one of the outer circumferential surface and the inner circumferential surface of the connection part is circular in cross section, facilitating connection between the inner hole of the hollow needle and the collected blood holding passage. Furthermore, when the puncture member and the blood holding member are connected to each other by, for example, fitting or press-fitting, a gap can be prevented at the potentially problematic corners and sides of a rectangular connection part. Thus, a gap can be suppressed at the connected portion between the puncture member and the blood holding member. Hence, a blood passage including the inner hole of the hollow needle and the collected blood holding passage is provided with higher airtightness from an external space. This can prevent problems such as unexpected leakage of blood and blood oxidization caused by exposure to outside air and secure a small amount of collected blood.

In the blood collection instrument according to the third preferred embodiment, preferably, the connection part, whose outer circumferential surface is circular in cross section, projects outward at the inflow port portion of the collected blood holding passage, and the puncture member is connected to be fit externally onto the connection part.

According to the blood collection instrument of the present preferred embodiment, the puncture member can be easily connected to the connection part, and when a tube or the like on the puncture member side is connected to the connection part, it is difficult for a gap to be formed between the tube and the connection part. When an elastic tube or the like, in particular, is connected to be fit externally onto the connection part, the circular outer circumferential surface of the connection part is easily fit onto the overall inner circumferential surface of the tube, thereby preventing leakage of blood at the connected portion.

A fourth preferred embodiment provides the blood collection instrument according to any one of the first to third preferred embodiments, wherein the blood collection instrument is used as a blood collection instrument for small animals.

The blood collection instrument according to the first to third preferred embodiments can be preferably used when a small amount of blood is collected from a small animal.

A fifth preferred embodiment provides a blood collection plate comprising: a blood holding member having a structure in which a plurality of plate-shaped members are overlapped with each other, the blood holding member including a collected blood holding passage formed between overlapped surfaces of the plurality of plate-shaped members; and a connection part provided at an inflow port portion of the collected blood holding passage in the blood holding member, the connection part being configured to connect with a puncture member including a hollow needle for puncture.

According to the blood collection plate of the present preferred embodiment, the puncture member having the hollow needle can be easily connected to the connection part at the inflow port portion of the collected blood holding passage, and the inner hole of the hollow needle is allowed to communicate with the collected blood holding passage. Thus, as compared with the conventional art, problems such as exposure of blood to the atmosphere during collection and oxidization associated with the exposure can be reduced or avoided.

A sixth preferred embodiment provides the blood collection plate according to the fifth preferred embodiment, wherein the connection part projects outward, and an outer circumferential shape of the connection part has a circular cross section.

According to the blood collection plate of the present preferred embodiment, the outer circumferential surface of the connection part is circular in cross section. Hence, when the puncture member and the blood holding member are connected to each other by, for example, fitting or press-fitting, a gap is not formed at the potentially problematic corners and sides of a rectangular connection part. Thus, a gap can be suppressed at the connected portion. Hence, a blood passage including the inner hole of the hollow needle and the collected blood holding passage is provided with higher airtightness from an external space. This can prevent problems such as unexpected blood leakage caused by a blood pressure or the like and blood oxidization caused by exposure to outside air and secure a small amount of collected blood.

A seventh preferred embodiment provides the blood collection plate according to the fifth or sixth preferred embodiment, wherein the connection part is integrated with one of the plurality of plate-shaped members.

According to the blood collection plate of the present preferred embodiment, as compared with the connection part formed over the plurality of plate-shaped members, it is difficult for a step or the like caused by overlapping the plate-shaped members to be formed on the surface of the connection part, and the surface of the connection part is easily smoothed. Hence, for example, if another member like the puncture member having the hollow needle is connected to the connection part, leakage of blood and exposure to outside air can be reduced at the connected portion.

An eighth preferred embodiment provides the blood collection plate according to any one of the fifth to seventh preferred embodiments, wherein the collected blood holding passage is formed in a noncircular shape in cross section between the overlapped surfaces of the plurality of plate-shaped members, and an inner hole of the connection part constituting the inflow port portion of the collected blood holding passage is more circularly shaped than the collected blood holding passage in cross section.

According to the blood collection plate of the present preferred embodiment, the collected blood holding passage formed between the overlapped surfaces of the plurality of plate-shaped members is more easily fabricated when being formed in a noncircular shape, e.g., a polygon in cross section than when being formed in a circular shape in cross section.

The inner hole of the connection part is nearly circle in cross section, thereby suppressing a reduction in the dimensional accuracy of members, the dimensional accuracy being reduced by heat shrinkage or the like during molding. Moreover, a uniform thickness enables accurate molding of the outer circumferential surface into a circular shape in cross section. Hence, when the puncture member or the like is fit externally onto the connection part, it is difficult for a gap to be formed at the connected portion.

A ninth preferred embodiment provides the blood collection plate according to any one of the fifth to eighth preferred embodiments, wherein the blood collection plate is used as a blood collection plate for small animals.

The blood collection plate according to the fifth to eighth preferred embodiments can be preferably used when a small amount of blood is collected from a small animal.

Effect of the Invention

According to the present invention, blood being collected can be prevented from being exposed to the atmosphere.

EMBODIMENTS FOR CARRYING OUT THE INVENTION

Embodiments of the present invention will be described below with reference to the accompanying drawings.

Figure 1:
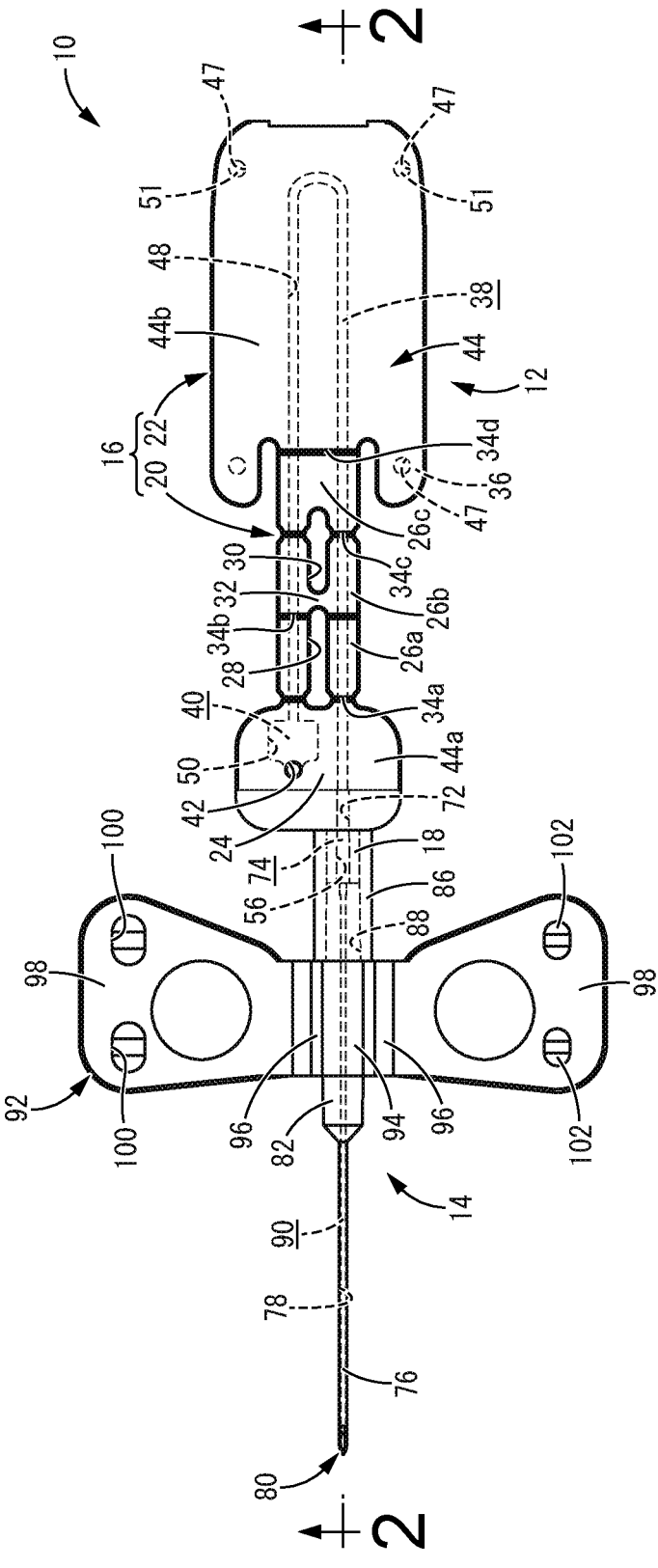
FIG. 1 is a plan view illustrating a blood collection instrument for small animals as a first practical embodiment of the present invention.
Figure 2:
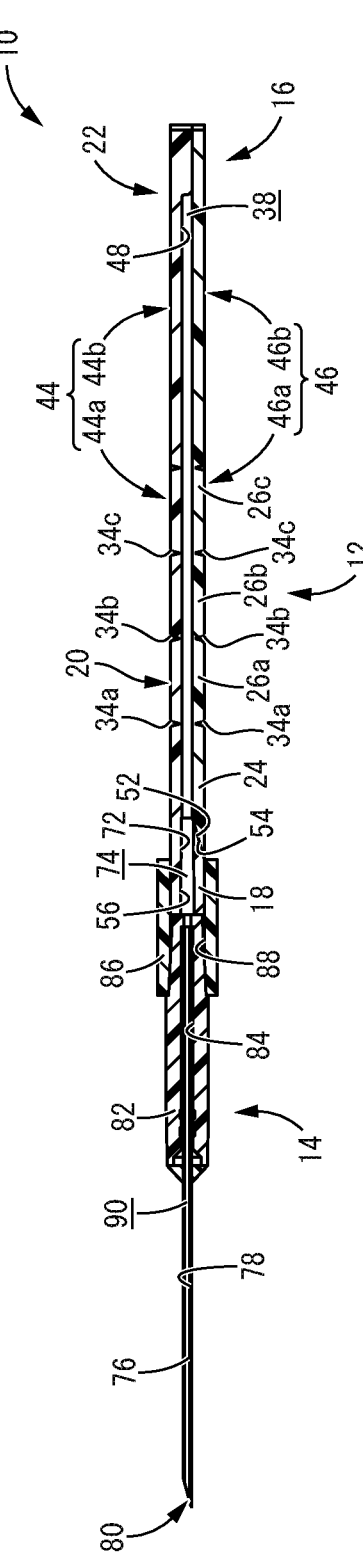
FIG. 2 is a cross-sectional view taken along line 2-2 of FIG. 1.

FIGS. 1 and 2 illustrate a blood collection instrument 10 for small animals as a first practical embodiment. The blood collection instrument 10 for small animals has a structure in which a puncture member 14 is attached to a blood collection plate 12 for small animals. In the following description, in principle, the distal end side denotes the left side in FIG. 1, that is, a needle tip 80 side of a hollow needle 76, which will be described later, and the proximal side denotes the right side in FIG. 1.

Figure 3:
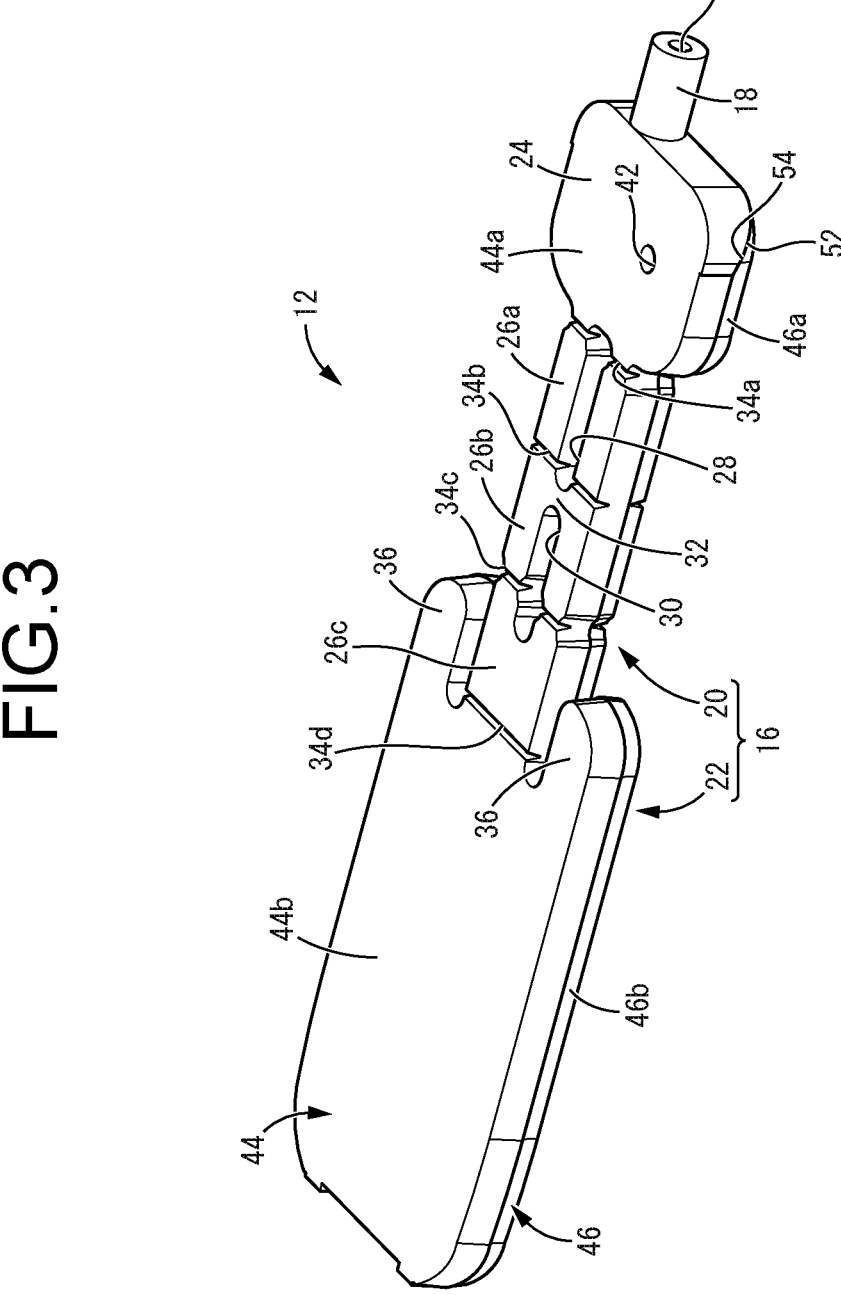
FIG. 3 is a perspective view of a blood collection plate for small animals, the blood collection plate constituting the blood collection instrument for small animals in FIG. 1.
Figure 4:
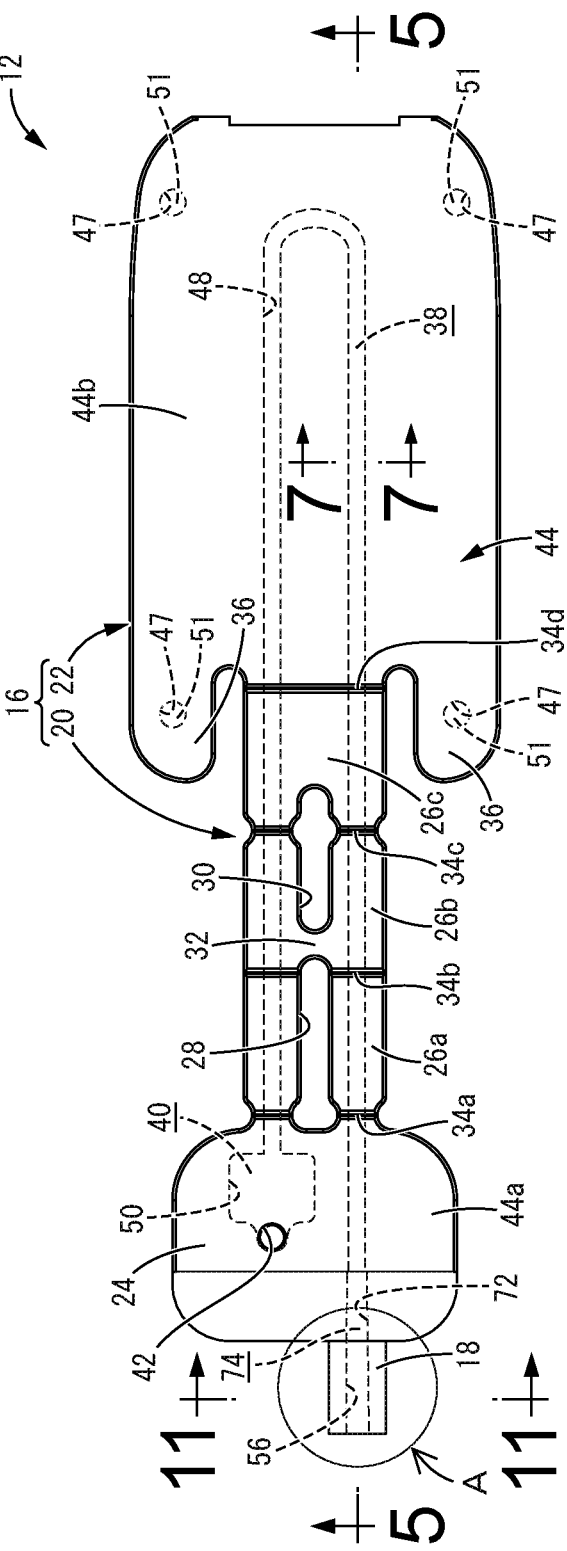
FIG. 4 is an enlarged plan view of the blood collection plate for small animals in FIG. 3.
Figure 5:
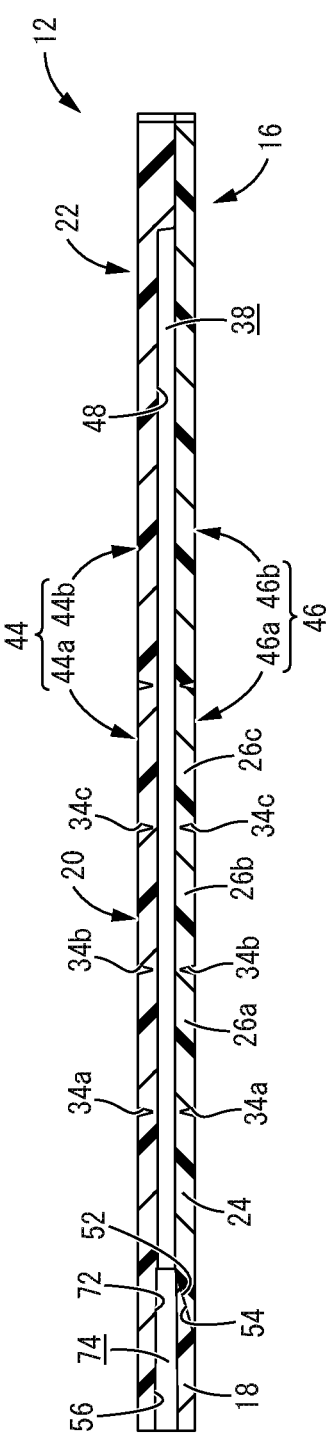
FIG. 5 is a cross-sectional view taken along line 5-5 of FIG. 4.

As illustrated in FIGS. 3 to 5, the blood collection plate 12 for small animals is entirely shaped like a plate and has a structure including a connection part 18 projecting from a blood holding member 16. The blood holding member 16 is provided with a collecting part 20 constituting a distal end portion and a blood cell recovering part 22 that constitutes a proximal end portion and recovers blood cells after centrifugal separation.

The collecting part 20 has an integrated structure of a platelike distal end part 24 and three extracting parts 26a, 26b, and 26c connecting the distal end part 24 and the blood cell recovering part 22. The distal end part 24 has a larger width than the extracting parts 26a to 26c and is shaped like a substantially square plate with rounded corners.

The extracting part 26a connecting to the distal end part 24 is split in the width direction by a slit 28 formed at the central portion in the width direction (in the vertical direction in FIG. 4), and portions disposed on both sides of the slit 28 in the width direction are substantially shaped like square poles. The extracting part 26b at an intermediate position in the longitudinal direction (the lateral direction in FIG. 4) in the collecting part 20 has the slit 28 and a slit 30 at the central portion in the width direction, and portions on both sides of the slits 28, 30 in the width direction are linked by a linking portion 32 provided between the slits 28, 30. The extracting part 26c connecting to the blood cell recovering part 22 has the distal end portion on both sides of the slit 30 in the width direction and is substantially shaped like a rectangular plate on the proximal end side of the slit 30.

At a connected portion between the distal end part 24 and the extracting part 26a, a cutting groove 34a is formed. At a connected portion between the extracting part 26a and the extracting part 26b, a cutting groove 34b is formed. At a connected portion between the extracting part 26b and the extracting part 26c, a cutting groove 34c is formed. At a connected portion between the extracting part 26c and the blood cell recovering part 22, a cutting groove 34d is formed. The cutting grooves 34a to 34d are formed on both surfaces of the blood holding member 16 in the thickness direction and linearly extend in the width direction of the blood holding member 16. The collecting part 20 has small cross-sectional areas at the portions where the cutting grooves 34a to 34d are formed. Thus, the collecting part can be bent with a hand at the portions where the cutting grooves 34a to 34d are formed. This can easily separate any one of the extracting parts 26a to 26c.

Both end portions of the slit 28 in the longitudinal direction reach the connected portion between the distal end part 24 and the extracting part 26a and the connected portion between the extracting part 26a and the extracting part 26b, and the cutting grooves 34a and 34b are each separated by the slit 28. The slit 30 is provided over the connected portion between the extracting part 26b and the extracting part 26c, and the cutting groove 34c is separated by the slit 30. With this configuration, the connected portion between the distal end part 24 and the extracting part 26a, the connected portion between the extracting part 26a and the extracting part 26b, and the connected portion between the extracting part 26b and the extracting part 26c are reduced in cross-sectional area by the slits 28, 30 as well as the cutting grooves 34a to 34c.

As illustrated in FIGS. 3 and 4, the blood cell recovering part 22 is entirely shaped like a substantially square plate with rounded corners and has a larger width than the collecting part 20. The blood cell recovering part 22 has a larger area than the collecting part 20, so that the blood cell recovering part 22 is sized to be easily operated with fingers. Furthermore, the blood cell recovering part 22 has a large surface area, allowing writing of identification information including the name, the identification number, and the date of collection of a sample or labeling of the identification information. In this way, the surface of the blood cell recovering part 22 can be used as an information display part for displaying necessary information.

On the distal end side of the blood cell recovering part 22, the extracting part 26c is integrally joined at the central portion in the width direction. At both end portions in the width direction on the distal end side of the blood cell recovering part 22, a pair of projecting parts 36 are separately disposed outside the extracting part 26c in the width direction. The length of the projecting part 36 is preferably shorter than that of the extracting part 26c and is longer than a half of the length of the extracting part 26c.

The blood holding member 16 contains a collected blood holding passage 38. The collected blood holding passage 38 has one end opened on the distal end face of the distal end part 24 of the collecting part 20, extends in the form of a letter U through the collecting part 20 and the blood cell recovering part 22, and has the other end allowed to communicate with a space part 40 provided in the distal end part 24. The collected blood holding passage 38 desirably has a small passage cross-sectional area that allows blood to pass through the passage by capillarity. Specifically, for example, the collected blood holding passage 38 has a width of 0.6 mm and a depth of 1 mm in cross section. The area and shape of the collected blood holding passage 38 may be changed in cross section.

The inner wall surface of the collected blood holding passage 38 is provided with an affinity for water by, for example, hydrophilization using surface treatment. The inner wall surface of the collected blood holding passage 38 is preferably coated with an anticoagulant that prevents coagulation of blood.

The collected blood holding passage 38 extends from the distal end part 24 to the blood cell recovering part 22 through the extracting parts 26a to 26c and is bent in the blood cell recovering part 22 to extend back to the distal end part 24 through the extracting parts 26a to 26c. Thus, in the extracting parts 26a to 26c, the collected blood holding passage 38 passes in the longitudinal direction through two points separated in the width direction. The collected blood holding passage 38 in the extracting part 26a, the collected blood holding passage 38 in the extracting part 26b, and the collected blood holding passage 38 in the extracting part 26c preferably have substantially the same capacity. The capacity of the collected blood holding passage 38 in the extracting parts 26a to 26c is properly set according to the kind of analysis conducted with collected blood. For example, in the case of quantitative analysis of blood, the collected blood holding passage 38 has a capacity of 10 μL in each of the extracting parts 26a to 26c.

The space part 40 allowed to communicate with the collected blood holding passage 38 has a larger cross-sectional area than the collected blood holding passage 38 and is sized not to allow the passage of blood by capillarity. A ventilation hole 42 is allowed to communicate with the space part 40. The ventilation hole 42 is opened on one surface of the distal end part 24, and the space part 40 is allowed to communicate with an external space through the ventilation hole 42.

Figure 6A:
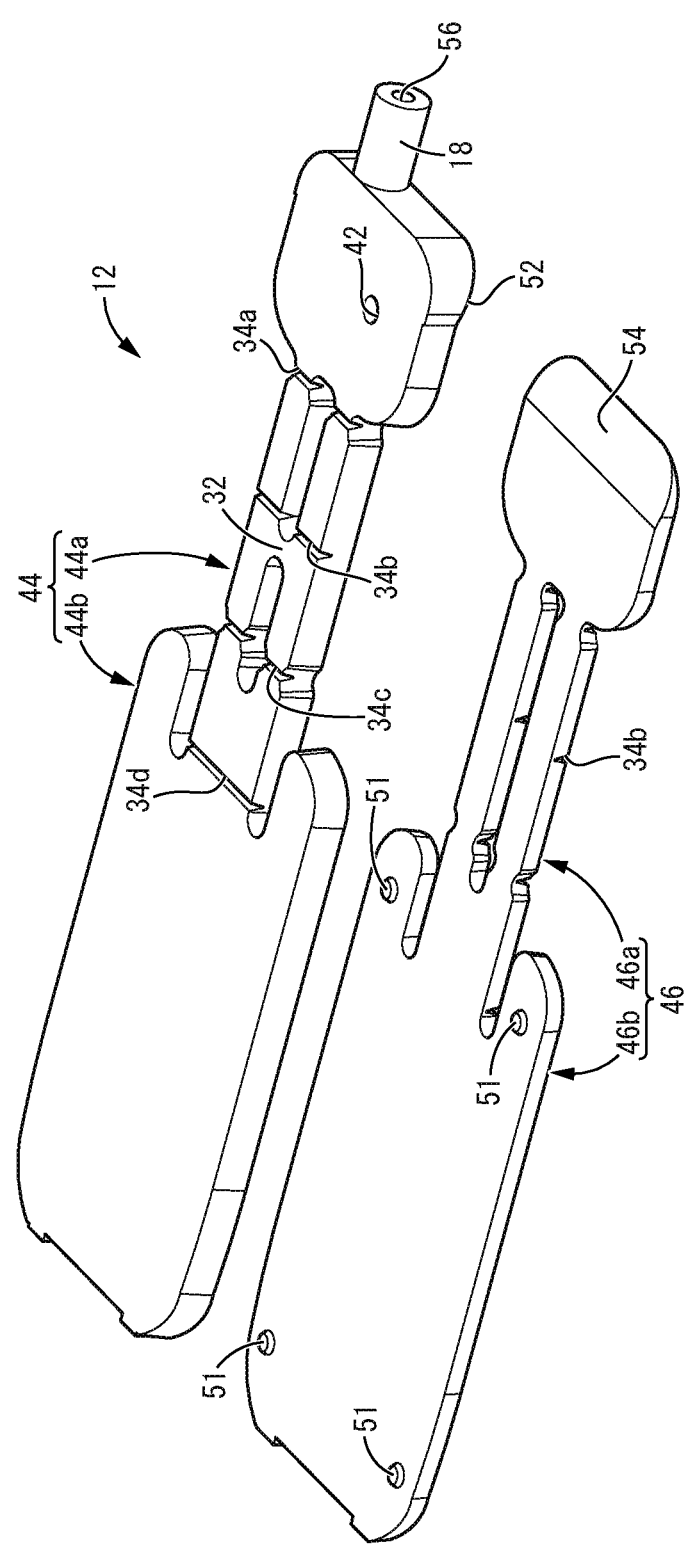
FIG. 6A is an exploded perspective view of the blood collection plate for small animals in FIG. 3.
Figure 6B:
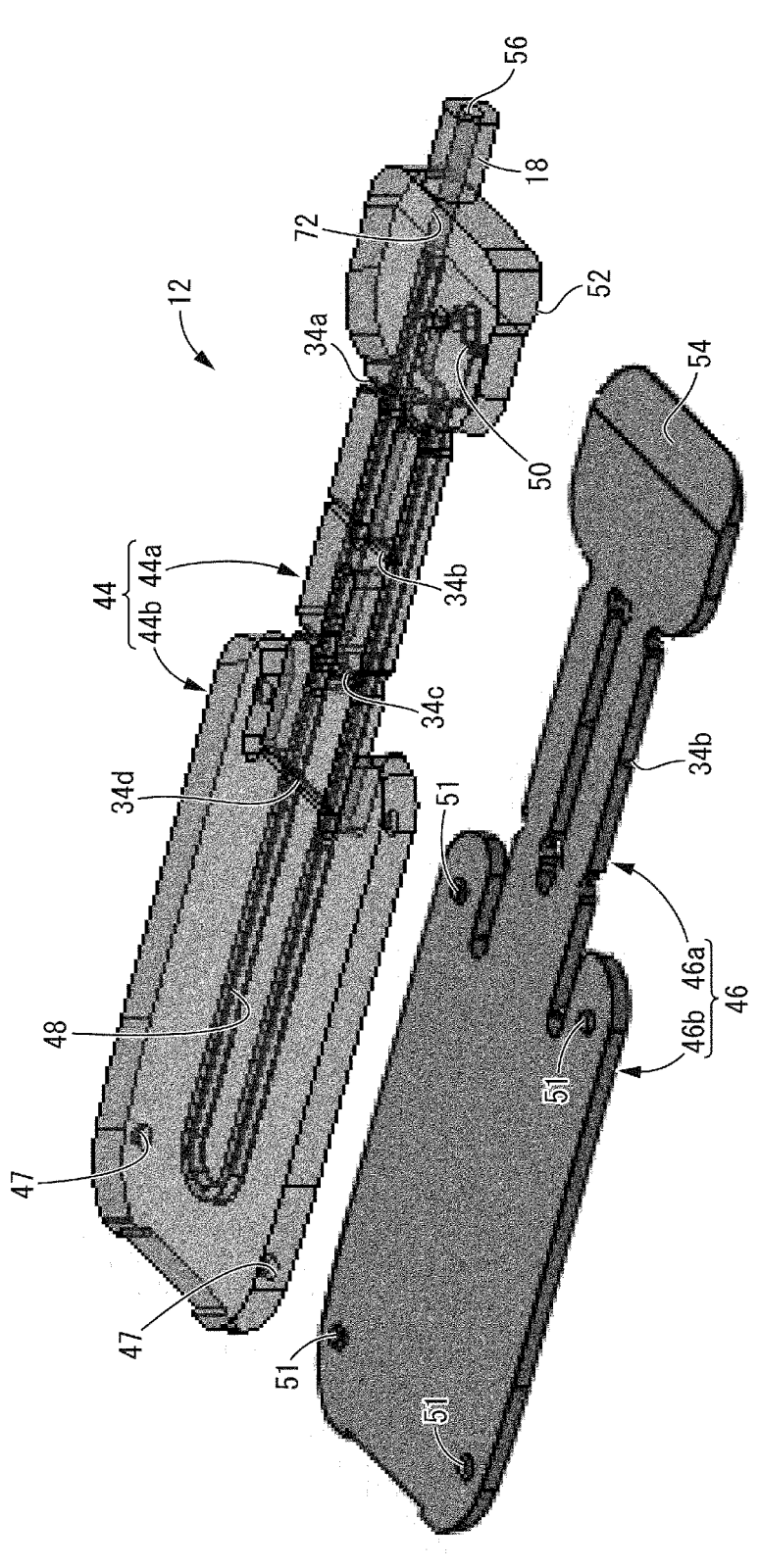
FIG. 6B is an exploded perspective view of the translucent blood collection plate for small animals in FIG. 6A.

The collected blood holding passage 38 and the space part 40 are formed between the overlapped surfaces of a first plate-shaped member 44 and a second plate-shaped member 46 that constitute the blood holding member 16. Specifically, as illustrated in FIGS. 6A and 6B, the blood holding member 16 including the collected blood holding passage 38 has a structure in which the first plate-shaped member 44 and the second plate-shaped member 46 are overlapped with each other. In FIG. 6A, for ease of viewing, the first plate-shaped member 44 and the second plate-shaped member 46 are illustrated as opaque members. In FIG. 6B, the first plate-shaped member 44 and the second plate-shaped member 46 are illustrated as translucent members in order to indicate the structure of the overlapped surface of the first plate-shaped member 44 with the second plate-shaped member 46.

The first plate-shaped member 44 includes a first narrow part 44a constituting the collecting part 20 and a first wide part 44b constituting the blood cell recovering part 22. The first plate-shaped member 44 has positioning concave parts 47 that are disposed at the four corner portions of the first wide part 44b and are opened on the overlapped surface of the first plate-shaped member 44 with the second plate-shaped member 46. The first plate-shaped member 44 has a concave groove 48 constituting the collected blood holding passage 38 and a recess 50 constituting the space part 40. The concave groove 48 and the recess 50 are opened on the surface of the first plate-shaped member 44 in the thickness direction. The concave groove 48 and the recess 50 both have noncircular cross sections and are substantially rectangular in cross section in the present practical embodiment. The ventilation hole 42 is formed as a through hole at the bottom wall part of the recess 50.

The second plate-shaped member 46 has a shape substantially corresponding to the first plate-shaped member 44 and includes a second narrow part 46a constituting the collecting part 20 and a second wide part 46b constituting the blood cell recovering part 22. The second plate-shaped member 46 has a smaller thickness than the first plate-shaped member 44. The second plate-shaped member 46 has positioning convex parts 51 that are disposed at the four corner portions of the second wide part 46b and are opened on the overlapped surface of the second plate-shaped member 46 with the first plate-shaped member 44.

The first plate-shaped member 44 and the second plate-shaped member 46 are preferably transparent or translucent, allowing the collected blood holding passage 38 formed between the first plate-shaped member 44 and the second plate-shaped member 46 to be visually recognized from the outside. It is particularly desirable to visually confirm the passage of blood through the collected blood holding passage 38 from the outside. The first plate-shaped member 44 and the second plate-shaped member 46 do not need to be entirely transparent or translucent, and visual recognition over the collected blood holding passage 38 from the outside is not always necessary. The first plate-shaped member 44 and the second plate-shaped member 46 may be opaque.

The first plate-shaped member 44 and the second plate-shaped member 46 are made of, for example, a synthetic resin such as cycloolefin polymer (COP), cycloolefin copolymer (COC), polymethyl methacrylate resin (PMMA), polypropylene resin (PP), polycarbonate resin (PC), and polyvinyl alcohol (PVA). COP and COC that exhibit an excellent transferring property during molding are preferably used.

The first plate-shaped member 44 and the second plate-shaped member 46 made of COP or COC are heated after surface treatment on the surfaces to be overlapped. The overlapped plate-shaped members are pressed to each other by a compressive force and thus are fixed to each other by chemical bonding. In the present practical embodiment, inclined surfaces 52, 54 are provided on the overlapped surfaces of the first plate-shaped member 44 and the second plate-shaped member 46. The inclined surfaces 52, 54 are overlapped with each other to position the first plate-shaped member 44 and the second plate-shaped member 46 in a direction perpendicular to the direction of overlapping. Specifically, the distal end portion of the first plate-shaped member 44 has the inclined surface 52 that is inclined in a direction along which the thickness of the plate-shaped member increases toward the distal end side, and the distal end portion of the second plate-shaped member 46 has the inclined surface 54 that is inclined in a direction along which the thickness of the plate-shaped member decreases toward the distal end side. As illustrated in FIG. 5, the inclined surface 52 of the first plate-shaped member 44 and the inclined surface 54 of the second plate-shaped member 46 are overlapped with each other, so that the first plate-shaped member 44 and the second plate-shaped member 46 are positioned in the longitudinal direction (the lateral direction in FIG. 5). The first plate-shaped member 44 and the second plate-shaped member 46 are positioned by the inclined surfaces 52, 54, thereby applying a compressive force in the direction of overlapping substantially over the overlapped portions of the first plate-shaped member 44 and the second plate-shaped member 46 so as to fix the overall plate-shaped members.

In order to position the first plate-shaped member 44 and the second plate-shaped member 46 in a direction perpendicular to the direction of overlapping of the plate-shaped members, stepped surfaces substantially parallel to the direction of overlapping may be provided instead of the inclined surfaces 52, 54. However, a force cannot be applied to the stepped surfaces in the pressing direction, so there is risk that the stepped surfaces may not be fixed with sufficient strength and may not maintain sufficient fluid tightness. In the absence of positioning structures such as the inclined surfaces 52, 54 and the stepped surfaces used instead of the inclined surfaces 52, 54, the first plate-shaped member and the second plate-shaped member are limited to the shapes of flat overlapped surfaces, and there is risk that during pressing in the direction of overlapping, the first plate-shaped member and the second plate-shaped member may be displaced relative to each other in the direction perpendicular to the direction of overlapping and bonded at an incorrect position.

Figure 7:
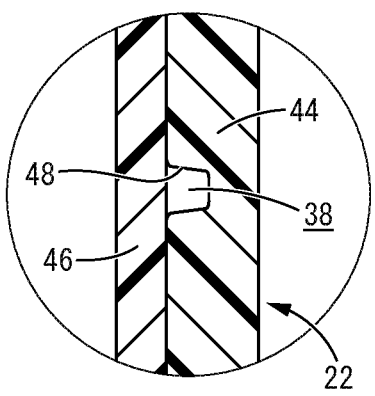
FIG. 7 is an enlarged cross-sectional view taken along line 7-7 of FIG. 4.

The first plate-shaped member 44 and the second plate-shaped member 46 are overlapped and fixed to each other, so that the openings of the concave groove 48 and the recess 50 on the first plate-shaped member 44 are covered with the second plate-shaped member 46. With this configuration, as illustrated in FIGS. 4 and 5, the collected blood holding passage 38 and the space part 40 are formed between the overlapped surfaces of the first plate-shaped member 44 and the second plate-shaped member 46 in the blood holding member 16. Since the concave groove 48 is substantially rectangular in cross section, as illustrated in FIG. 7, the collected blood holding passage 38, which is formed by covering the opening of the concave groove 48 with the flat surface, is formed in a noncircular shape in cross section. In the present practical embodiment, the collected blood holding passage 38 is substantially rectangular in cross section. Likewise, since the recess 50 is substantially rectangular in cross section, the space part 40, which is formed by covering the opening of the recess 50 with the flat surface, is substantially rectangular in cross section.

The connection part 18 is integrated with the first plate-shaped member 44 constituting the blood holding member 16. As illustrated in FIGS. 8 to 11, the connection part 18 is substantially cylindrical and projects from the distal end part 24 of the blood holding member 16 toward the distal end side. An inner hole 56 of the connection part 18 is allowed to communicate with the collected blood holding passage 38. The collected blood holding passage 38 is opened to an external space through the inner hole 56. Like the collected blood holding passage 38, the inner hole 56 of the connection part 18 is a small-diameter hole that allows blood to pass through the inner hole by capillarity. The inner hole 56 of the connection part 18 is more circularly shaped than the collected blood holding passage 38 in cross section. In the present practical embodiment, the inner hole 56 is substantially circular in cross section. In short, the connection part 18 of the present practical embodiment has the outer circumferential surface and the inner circumferential surface that are both substantially cylindrical.

Figure 12:
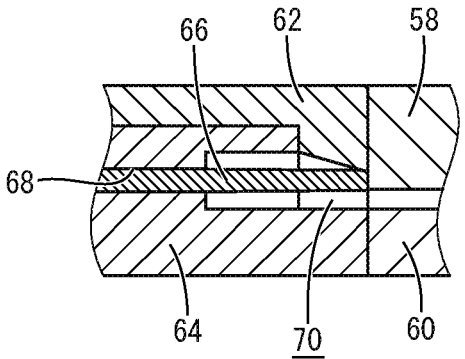
FIG. 12 is a principal-part cross-sectional view illustrating the process of manufacturing a first plate-shaped member constituting the blood collection plate for small animals in FIG. 3.

The outer circumferential surface of the connection part 18 is substantially shaped like a smooth cylinder free of asperities such as parting lines formed during molding. As illustrated in FIG. 12, on the proximal end side behind the inclined surface 52 of the distal end part 24, the first plate-shaped member 44 provided with the connection part 18 is molded by proximal end split molds 58, 60 divided in the thickness direction. Furthermore, on the first plate-shaped member 44, a portion having the inclined surface 52 of the distal end part 24 and the connection part 18 are molded by a distal end split mold 62 that is movable in the thickness direction and molds the inclined surface 52, a slide mold 64 movable in the longitudinal direction, and a pin mold 66 movable in the longitudinal direction relative to the slide mold 64.

The slide mold 64 molds the distal end face of the distal end part 24 and the backside facing the inclined surface 52 and includes a cylindrical through hole 68 extending in the longitudinal direction. At the center of the through hole 68, the pin mold 66 for molding the inner hole 56 of the connection part 18 is inserted from the distal end side. The end face of the proximal end side of the pin mold 66 is projected onto the molding portion of the concave groove 48 in the proximal end split mold 58 in the longitudinal direction.

Thereafter, a synthetic resin material is injected into a cavity 70 formed by combining the proximal end split molds 58, 60, the distal end split mold 62, the slide mold 64, and the pin mold 66 and is molded therein, thereby forming the first plate-shaped member 44.

The outer circumferential surface of the connection part 18 is molded by the inner wall surface of the through hole 68 and thus has no parting lines. The inner hole 56 of the connection part 18 is molded by the pin mold 66 and thus the inner circumferential surface of the connection part 18 has no parting lines.

A portion where the inclined surface 52 is formed in the distal end part 24 is molded by the distal end split mold 62, the slide mold 64, and the pin mold 66 and thus the portion has a tunnel-like passage 72 that is allowed to communicate with the inner hole 56 of the connection part 18. The proximal end part of the tunnel-like passage 72 is allowed to communicate with the collected blood holding passage 38. The inner hole 56 of the connection part 18 and the tunnel-like passage 72 constitute an inflow port 74. In the present practical embodiment, the inflow port of the collected blood holding passage 38 in the blood holding member 16 is configured with the tunnel-like passage 72, and the inflow port in the connection part 18 is configured with the inner hole 56. Thus, the connection part 18 is projected at the inflow port portion of the collected blood holding passage 38 in the blood holding member 16.

As illustrated in FIGS. 1 and 2, the puncture member 14 is attached to the blood collection plate 12 for small animals having the foregoing structure. The puncture member 14 has a hollow needle 76 for puncture. The hollow needle 76 is made of stainless steel or the like and has an inner hole 78 penetrating from the distal end to the proximal end. The hollow needle 76 has a needle tip 80 with a sharply tapering shape at the distal end portion.

The proximal end part of the hollow needle 76 is joined to a needle hub 82. The needle hub 82 is substantially cylindrical, and the proximal end part of the hollow needle 76 is inserted to be connected to the needle hub 82. An inner hole 84 of the needle hub 82 is allowed to communicate with the inner hole 78 of the hollow needle 76. A connection tube 86 serving as a connection linking part is attached to the proximal end part of the needle hub 82. The connection tube 86 is made of synthetic resin or the like with flexibility and is fit externally onto the proximal end part of the needle hub 82 by a user. For the connection tube 86, a synthetic resin as a base material (material) different from that of the blood collection plate 12 for small animals, for example, soft polyvinyl chloride and an elastomer are preferably used because flexibility is obtained. The connection tube 86 may be provided with flexibility by reducing the thickness of the connection tube 86 relative to the thickness of the connection part 18 other than varying the base materials between the blood collection plate 12 for small animals and the connection tube 86. The inside diameter of the connection tube 86 is preferably smaller than the outside diameter of the connection part 18. Leakage of blood can be reduced by eliminating a gap between the connection tube 86 and the connection part 18. Also, the inside diameter of the connection tube 86 may be slightly increased toward the proximal end side such that the connection part 18 is easily inserted. The initial shape of the connection tube 86 which is not deformed by an external force is substantially cylindrical, and its inner circumferential surface, in particular, is a substantially cylindrical surface. The inner circumferential surface of the connection tube 86 has a smaller diameter than the outer circumferential surface of the connection part 18. The connection tube 86 is preferably transparent or translucent, allowing visual confirmation of a blood flow into an inner hole 88 from the outside. In the puncture member 14, an internal passage 90 that continues in the longitudinal direction is formed by the inner hole 78 of the hollow needle 76, the inner hole 84 of the needle hub 82, and the inner hole 88 of the connection tube 86. The needle hub 82 and the connection tube 86 may be fit to each other in an unbonded manner, fixed to each other with an adhesive or the like, or formed in an integrated manner.

In the present practical embodiment, the needle hub 82 has a wing-like part 92. The wing-like part 92 is made of, for example, a soft synthetic resin. The wing-like part 92 has plate-like linking parts 96, 96 formed to integrally protrude from a cylindrical fitting tube part 94 in the tangential direction of the fitting tube part 94, and a wing main body 98 is integrally formed on each of the protruding distal end sides of the linking parts 96, 96 protruding from the fitting tube part 94. The wing-like part 92 is attached to the needle hub 82 by fixing the fitting tube part 94 to be fit externally onto the needle hub 82.

For example, the wing-like part 92 is deformed to overlap the pair of wing main bodies 98, 98, and the overlapped wing main bodies 98, 98 are pinched with fingers, so that the small-diameter puncture member 14 can be easily held. Moreover, puncture is stabilized by holding the wing main bodies 98, 98. Since the hollow needle 76 and the wing main bodies 98, 98 are fixed, the bevel of the hollow needle 76 is easily directed to the ceiling and easily punctures a small object like a tail when a small animal is punctured with the hollow needle 76. It is also expected that puncture more parallel to a surface of a small animal is easily performed, reducing pain afflicted. The pair of wing main bodies 98, 98 has concave parts 100, 100 and convex parts 102, 102 that are located at corresponding positions. When the wing main bodies 98, 98 are mutually overlapped and pinched, the convex parts 102 are fit into the concave parts 100 so as to align the wing main bodies 98, 98 in parallel with the overlapped surfaces.

The puncture member 14 is connected to the blood collection plate 12 for small animals. Specifically, the blood collection plate 12 for small animals and the puncture member 14 are connected to each other by fitting the connection tube 86 of the puncture member 14 externally onto the connection part 18 of the blood collection plate 12 for small animals. This allows the collected blood holding passage 38 of the blood collection plate 12 for small animals to communicate with the internal passage 90 of the puncture member 14 through the inner hole 56 of the connection part 18. The passage cross-sectional area of the internal passage 90 may be equal to or different from the cross-sectional areas of the collected blood holding passage 38 and the inner hole 56. The time for collecting blood can be reduced by increasing the passage cross-sectional area of the internal passage 90.

The blood collection instrument 10 for small animals with the puncture member 14 connected to the blood collection plate 12 for small animals is used by, for example, puncturing a small animal with the hollow needle 76 of the puncture member 14. Blood having flowed into the internal passage 90 from the needle tip 80 of the inserted hollow needle 76 is passed through the inner hole 56 of the connection part 18 and the collected blood holding passage 38 by a blood pressure. A this point, along with the passage of blood, air in the internal passage 90, the inner hole 56 of the connection part 18, and the collected blood holding passage 38 is ejected to the outside through the ventilation hole 42 allowed to communicate with the space part 40. This can prevent air in the inner hole 56 of the connection part 18 and the collected blood holding passage 38 from interfering with the passage of blood.

When the collected blood holding passage 38 is entirely filled with blood, capillarity does not cause the passage of blood in the space part 40 having a large cross-sectional area, and thus a blood flow is decelerated or stopped. After the arrival of blood at the connected portion of the collected blood holding passage 38 and the space part 40 is confirmed, the hollow needle 76 is removed from the small animal, thereby collecting a predetermined amount of blood in the collected blood holding passage 38.

After the hollow needle 76 is removed, the blood collection plate 12 for small animals is detached from the puncture member 14. After the detachment from the puncture member 14, the blood collection plate 12 for small animals can be entirely attached to, for example, a holder for a centrifuge and can be used for processing such as centrifugation.

Alternatively, at least one of the cutting grooves 34a to 34d can be bent and cut with fingers and blood collected in at least one of the extracting parts 26a to 26c can be used as a sample for analysis. The extracting part 26a is divided in the width direction by the slit 28, and thus a half amount of blood in the extracting parts 26b, 26c can be obtained as a sample. In the extracting part 26b, the linking portion 32 only includes the first plate-shaped member 44 and has a small cross-sectional area. Thus, the linking portion 32 can be bent and cut. With this configuration, also in the extracting part 26b, a half amount of blood in the extracting part 26c can be obtained as a sample. Furthermore, blood collected in the distal end part 24 and the blood cell recovering part 22 can be also used as a sample.

The blood collection instrument 10 for small animals with the structure of the present practical embodiment allows puncture on a small animal with the hollow needle 76 to guide blood in a blood vessel into the collected blood holding passage 38 without exposing the blood to an external space. Hence, as compared with the conventional method of collecting blood from a drop of blood in the atmosphere, it is difficult for blood to be oxidized and a proper sample can be obtained.

Moreover, the present practical embodiment eliminates the need for training or the like for forming a drop of blood in a size suitable for collection. Furthermore, the present practical embodiment also eliminates the complicated work of switching to an instrument for collecting blood after the puncture with a puncture needle to form a drop of blood.

In the blood collection plate 12 for small animals, the outer circumferential surface of the connection part 18 connected to the puncture member 14 is a smooth cylindrical surface free of asperities such as parting lines. Thus, when the connection tube 86 is fit externally onto the connection part 18, it is difficult for a gap to be formed between the connection tube 86 and the connection part 18, thereby preventing leakage of blood at the connected portion between the blood collection plate 12 for small animals and the puncture member 14. Furthermore, the connection tube 86 has flexibility and thus easily comes into intimate contact with the outer circumferential surface of the connection part 18, so that it is more difficult for a gap to be formed between the connection tube 86 and the connection part 18.

The conventional blood collection plate for small animals has a structure in which plate-shaped members are entirely bonded to each other. Thus, the outer circumferential surface of the connection part is rectangular in cross section. Even if the connection tube 86 has flexibility, a gap may appear at the corners and sides of the connection part. For example, some animals such as a mouse have substantially the same blood pressure as a human and thus blood may leak from the gap. However, in the blood collection plate 12 for small animals according to the present practical embodiment, the outer circumferential surface of the connection part 18 is circular in cross section. Thus, the connection tube 86 almost evenly comes into intimate contact with the entire outer circumferential surface of the connection part 18 and it is difficult for a gap to be formed between the connection part 18 and the connection tube 86.

The connection tube 86 of the puncture member 14 attached to the connection part 18 of the blood collection plate 12 for small animals has elasticity. The connection tube 86 is placed onto the connection part 18 while being deformed to a larger diameter, thereby easily connecting the blood collection plate 12 for small animals and the puncture member 14. Moreover, the connection tube 86 is fit onto the connection part 18 with elasticity, and thus the blood collection plate 12 for small animals and the puncture member 14 can be easily separated only by drawing the connection part 18 from the connection tube 86.

The provision of the flexible connection tube 86 between the blood collection plate 12 for small animals and the puncture member 14 reduces the transmission of force between the blood collection plate 12 for small animals and the puncture member 14. Thus, for example, even if an external force is applied with a hand to the blood collection plate 12 for small animals at the time of puncture on a small animal with the puncture member 14, the transmission of the external force to the puncture member 14 is reduced by the deformation of the connection tube 86, avoiding problems such as an unintended cut on the cutting groove.

The blood collection plate 12 for small animals has a structure in which the first plate-shaped member 44 and the second plate-shaped member 46 are overlapped and fixed to each other, and the collected blood holding passage 38 is formed between the overlapped surfaces of the first plate-shaped member 44 and the second plate-shaped member 46. Hence, the collected blood holding passage 38 can be easily formed, and the collected blood holding passage 38 can be obtained with accuracy in shape and dimensions.

The connection part 18 is integrated with the first plate-shaped member 44. Thus, as compared with a plurality of members constituting a connection part in cooperation, the outer circumferential surface of the connection part 18 is likely to be smoothly molded and it is difficult for a gap to be formed between the connection part 18 and the connection tube 86. In particular, even if a small displacement occurs in parallel with the bonding surface at the time of bonding between the first plate-shaped member 44 and the second plate-shaped member 46, the displacement does not affect the shape of the outer circumferential surface of the connection part 18.

The inner hole 56 of the connection part 18 is more circularly shaped than the collected blood holding passage 38 in cross section. Hence, when the connection part 18 is molded, the accuracy of dimensions of the connection part 18 can be easily secured against deformation caused by heat shrinkage during molding. If the inner circumferential surface of the connection part 18 has large non-circularity in cross section, the outer circumferential surface of the connection part 18 is also likely to be distorted. Thus, in the present practical embodiment, the inner circumferential surface is formed in a substantially circular shape in cross section, thereby smoothing the outer circumferential surface and reducing a gap between the connection part 18 and the connection tube 86.

Figure 8:
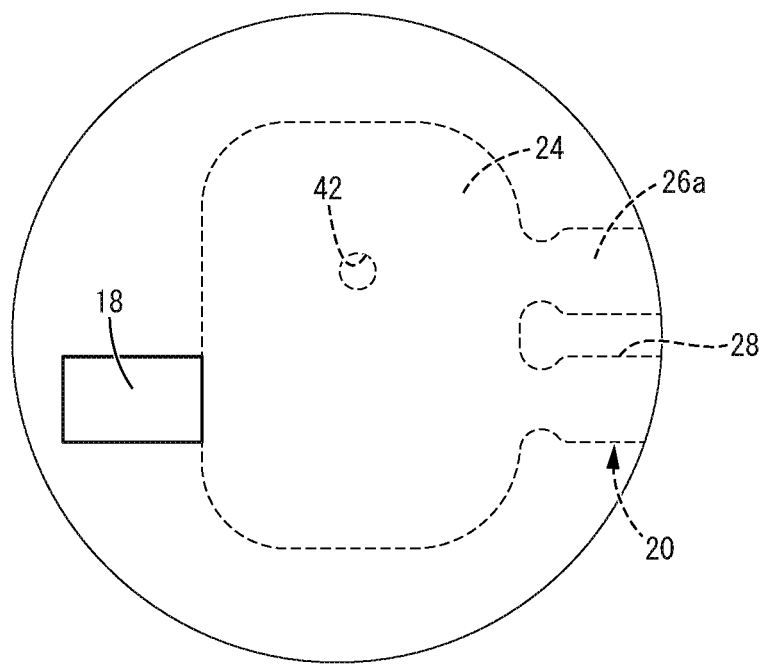
FIG. 8 is an enlarged view of an A part of FIG. 4.
Figure 9:
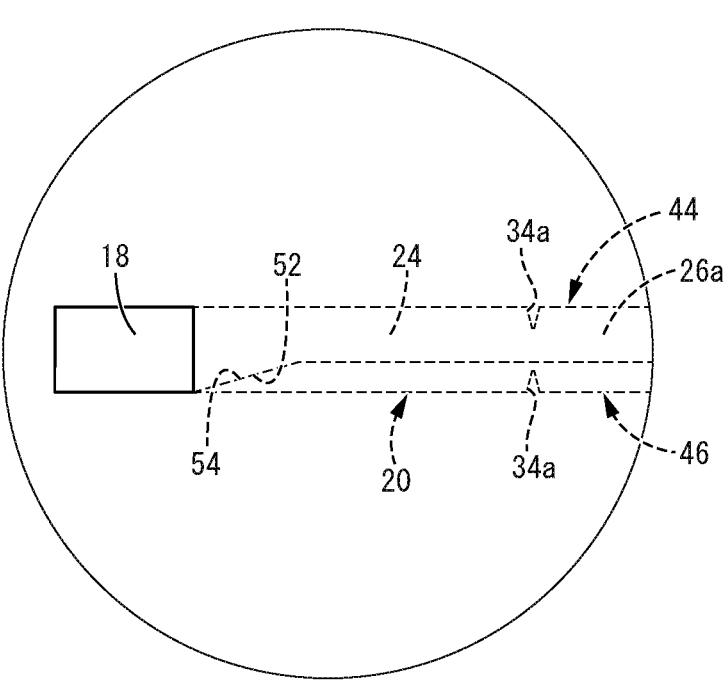
FIG. 9 is a bottom view of FIG. 8.
Figure 10:
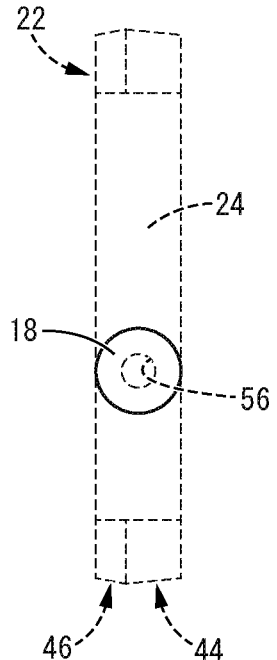
FIG. 10 is a left side view of FIG. 8.
Figure 11:
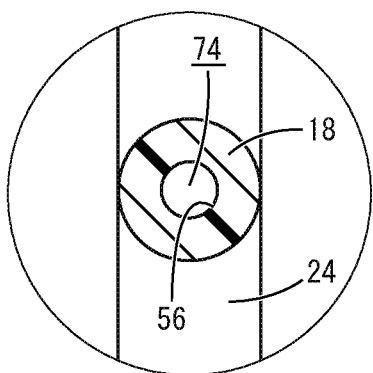
FIG. 11 is an enlarged cross-sectional view taken along line 11-11 of FIG. 4.

As illustrated in FIGS. 8 to 10, the connection part 18 has the substantially cylindrical outer circumferential surface and projects from the plank-shaped blood holding member 16 toward the distal end side. Thus, the connection part 18 is recognized as a part devised as a design. The connection part 18 has the specific function of connecting the puncture member 14 and has the substantially cylindrical outer circumferential surface, achieving the effect of preventing the formation of a gap at the connected portion and preventing leakage of blood when the puncture member 14 is connected to be fit externally onto the connection part 18. Furthermore, the connection part 18 has a special design, which is the substantially cylindrical outer circumferential surface, on a plate part formed by bonding plates, thereby attracting attention from persons who perceive the connection part 18 and arousing an aesthetic sense of the persons.

The practical embodiment of the present invention was specifically described, but the present invention is not limited by the specific description. For example, the number of extracting parts 26 may be one, two, or four or more. It is preferable to provide the multiple extracting parts 26 that enable multiple quantitative analyses at one-time collection of blood. In the case of the multiple extracting parts 26, the extracting parts 26 may be allowed to hold different volumes of blood.

The blood holding member 16 can be also formed by overlapping three or more plate-shaped members with one another. For example, if three or more plate-shaped members are overlapped, a collected blood holding passage can be formed by forming a slit on the intermediate plate-shaped member and covering the opening of the slit with the two plate-shaped members on both sides of the intermediate plate-shaped member. Alternatively, a collected blood holding passage may be formed with a tunnel structure partially on one plate-shaped member.

The practical embodiment described the method of fixing the plate-shaped members 44, 46 formed by COP or COC. However, the fixing method of the practical embodiment is merely exemplary. For example, according to the material or the like of the plate-shaped members, the fixing method can be properly changed to laser welding, bonding by activating the bonded surfaces, bonding with an adhesive, or the like.

The connection part 18 of the practical embodiment is integrated with the one plate-shaped member 44, but the connection part may be configured with a plurality of plate-shaped members in cooperation. Specifically, for example, a cylindrical connection part can be also formed by overlapping and fixing the first plate-shaped member 44 having an upper half portion of the connection part and the second plate-shaped member 46 having a lower half portion. In this case, a step may be formed on the outer circumferential surface of the connection part by overlapping the plate-shaped members. However, if the connection tube 86 is made of a material having properly adjusted hardness and elasticity, a gap can be reduced such that liquid leakage is unlikely to occur. Moreover, asperities such as a step can be also absorbed by providing a cap member, which has no asperities on the outer circumferential surface, on the outer circumferential surface of the connection part. For example, the cap member may be a separate member from the connection part and capped onto the outer circumferential surface of the connection part or may be integrally molded on the outer circumferential surface of the connection part by multicolor molding.

The connection part is not limited to a part integrated with the plate-shaped member. For example, the connection part may be a separate component from the plate-shaped member and attached to the distal end portion of the plate-shaped member. If a cylindrically projecting connection part is used, a recess may be provided to open on a surface of the plate-shaped member and the connection part may be formed in the recess so as to project from the bottom of the recess.

For example, the connection part may have a surface to be fit to the connection linking part of the puncture member 14 such that the surface has any shape other than a circle in cross section. Thus, the connection part is not limited to a cylindrical shape.

In the present practical embodiment, the connection tube 86 of the puncture member 14 is connected to be fit externally onto the connection part 18 of the blood collection plate 12 for small animals. However, for example, the connection linking part of the puncture member may be fit into the connection part to connect the puncture member to the connection part. In this case, the connection part does not always need to project from the blood holding member toward the distal end side. For example, the connection part may be configured with a hole that is opened on the distal end face of the blood holding member such that the puncture member is fit into the hole.

The blood collection plate 12 for small animals and the puncture member 14 are desirably connected so as to be separable from each other but may be inseparably connected to each other. For example, during molding of the blood collection plate 12 for small animals, the hollow needle 76 may be fixedly connected to the blood collection plate 12 for small animals with an adhesive or by insert molding. Alternatively, the connection tube 86 of the puncture member 14 may be fixed to the connection part 18 of the blood collection plate 12 for small animals by means including bonding and welding. The connection between the connection tube 86 of the puncture member 14 and the blood collection plate 12 for small animals may be a connection made by screwing with a screw structure. Moreover, at the time of puncture, holding the blood collection plate 12 for small animals leads to difficulty in a puncture operation. Thus, a holding cylindrical part to be pinched on both sides with fingers or a wing part is preferably provided on the distal end side with respect to the blood collection plate 12 for small animals. A plate-shaped blood cell holding part, in particular, is likely to come into contact with a palm or the like because of the shape of the holding part. Thus, by providing a wing part at a position separated from the blood cell holding part, a hand becomes less likely to come into contact with the blood collection plate 12 for small animals at the time of puncture. If the blood collection plate 12 for small animals and the puncture member 14 are inseparably connected, the holding portion of collected blood can be separated from the puncture member 14 by, for example, cutting and separating the distal end part 24 and the extracting part 26a of the blood collection plate 12 for small animals after blood collection is completed.

The connection linking part for connecting the blood collection plate 12 for small animals and the puncture member 14 is desirably a flexible member like the connection tube 86 described in the practical embodiment. However, the connection linking part is not limited thereto. Also, the connection linking part may be formed as a single member or include multiple members.

The puncture member 14 is provided with the wing-like part 92 that can be pinched with fingers, allowing the puncture member 14 to be easily held so as to facilitate a puncture operation. However, the wing-like part 92 is not always necessary. For example, a holding surface to be pinched with fingers may be provided on the side of the needle hub 82 of the puncture member 14 such that the needle hub 82 is held on the holding surface, or puncture can be also performed on a small animal while holding the blood cell recovering part 22 of the blood collection plate 12 for small animals, the blood collection plate 12 being connected to the puncture member 14.

The blood collection plate 12 for small animals is used for blood collection as the blood collection instrument 10 for small animals while being connected to the puncture member 14. Alternatively, as in the conventional art, blood can be collected by bringing the distal end of the inflow port 74 into contact with a drop of blood formed on a skin of a small animal. In this case, expanding parts such as a radially extending groove-like notch and a hole-like concave part can be also formed on the distal-end face of the connection part 18 such that blood can be smoothly collected from a drop of blood.

The practical embodiment described the blood collection instrument 10 and the blood collection plate 12 for small animals. However, the blood collection instrument and the blood collection plate according to the present invention are used not only for collecting blood from small animals but also for collecting blood from, for example, large animals and humans.

KEYS TO SYMBOLS

10 blood collection instrument for small animals (blood collection instrument)
12 blood collection plate for small animals (blood collection plate)
14 puncture member
16 blood holding member
18 connection part
20 collecting part
22 blood cell recovering part
24 distal end part
26 extracting part
28 slit
30 slit
32 linking portion
34 cutting groove
36 projecting part
38 collected blood holding passage
40 space part
42 ventilation hole
44 first plate-shaped member
44a first narrow part
44b first wide part
46 second plate-shaped member
46a second narrow part
46b second wide part
47 positioning concave part
48 concave groove
50 recess
51 positioning convex part
52 inclined surface 54 inclined surface
56 inner hole
58 proximal end split mold
60 proximal end split mold
62 distal end split mold
64 slide mold
66 pin mold
68 through hole
70 cavity
72 tunnel-like passage
74 inflow port
76 hollow needle
78 inner hole
80 needle tip
82 needle hub
84 inner hole
86 connection tube (connection linking part)
88 inner hole
90 internal passage
92 wing-like part
94 fitting tube part
96 linking part
98 wing main body
100 concave part
102 convex part

The invention claimed is:

1. A blood collection instrument comprising:
a blood holding member having a structure in which a plurality of plate-shaped members are overlapped with each other, the blood holding member including a collected blood holding passage formed between overlapped surfaces of the plurality of plate-shaped members;
a connection part provided at an inflow port portion of the collected blood holding passage in the blood holding member; and
a puncture member including a hollow needle for puncture, the puncture member being connected to the connection part, wherein
an inner hole of the hollow needle of the puncture member is allowed to communicate with the collected blood holding passage of the blood holding member,
the collected blood holding passage is formed in a non-circular shape in cross section between the overlapped surfaces of the plurality of plate-shaped members, and
an inner hole of the connection part constituting the inflow port portion of the collected blood holding passage is more circularly shaped than the collected blood holding passage in cross section.

2. The blood collection instrument according to claim 1, wherein the connection part projects outward, and a connection linking part on a hollow needle side that is connected to be fit externally onto the connection part has flexibility.

3. The blood collection instrument according to claim 1, wherein at least one of an outer circumferential surface and an inner circumferential surface of the connection part is circular in cross section.

4. The blood collection instrument according to claim 1, wherein the blood collection instrument is used as a blood collection instrument for small animals.

* * * * *